United States Patent
Arai

(10) Patent No.: US 9,303,239 B2
(45) Date of Patent: Apr. 5, 2016

(54) METHOD FOR CLEANING MICROFLUIDIC DEVICE AND CLEANING LIQUID

(71) Applicant: SHIMADZU CORPORATION, Kyoto-shi, Kyoto (JP)

(72) Inventor: Akihiro Arai, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 396 days.

(21) Appl. No.: 13/778,810

(22) Filed: Feb. 27, 2013

(65) Prior Publication Data

US 2014/0238444 A1    Aug. 28, 2014

(51) Int. Cl.
| | |
|---|---|
| *B08B 3/08* | (2006.01) |
| *B08B 3/04* | (2006.01) |
| *B08B 9/00* | (2006.01) |
| *C11D 7/50* | (2006.01) |
| *C11D 7/26* | (2006.01) |

(Continued)

(52) U.S. Cl.
CPC ............. *C11D 7/5022* (2013.01); *B08B 3/04* (2013.01); *B08B 3/08* (2013.01); *B08B 9/00* (2013.01); *C11D 7/265* (2013.01); *C11D 7/28* (2013.01); *C11D 7/34* (2013.01); *C11D 7/5004* (2013.01); *C11D 7/5013* (2013.01); *C11D 11/0023* (2013.01); *B01L 3/502753* (2013.01); *G01N 27/44791* (2013.01); *G01N 30/6095* (2013.01)

(58) Field of Classification Search
CPC ............. B08B 3/04; B08B 3/08; B08B 9/00; C11D 3/16
USPC .................... 134/22.14, 22.19, 42
See application file for complete search history.

(56) References Cited

U.S. PATENT DOCUMENTS

| 4,680,201 A | 7/1987 | Hjerten |
|---|---|---|
| 7,678,254 B2 | 3/2010 | Hanafusa et al. |

(Continued)

FOREIGN PATENT DOCUMENTS

| JP | 2000-137030 | * | 5/2000 |
|---|---|---|---|
| JP | 2000-137030 A | | 5/2000 |

(Continued)

OTHER PUBLICATIONS

Suzuki, Koichi et al., "MCE-202 "MultiNA": Microchip Electrophoresis System for DNA/RAN Analysis—Development and Application—", Shimadzu Review, 2007, vol. 64, No. 3 & 4, pp. 117-122.

(Continued)

*Primary Examiner* — Saeed T Chaudhry
(74) *Attorney, Agent, or Firm* — Cheng Law Group, PLLC

(57) ABSTRACT

The present invention provides a cleaning method by which the performance of a microchip can be recovered and a cleaning liquid. A method for cleaning a microfluidic device comprising: cleaning a channel that is formed in the microfluidic device, has a surface having a polymer coating, and has been brought into contact with a sample containing nucleic acid and/or protein, by bringing the channel into contact with a cleaning liquid comprised only of an organic solvent having solubility in at least the same volume of water at 25° C., or a cleaning liquid containing 50 vol % or more of the organic solvent in a buffer solution. The method wherein the buffer solution has a pH of 8 to 10. The method wherein the buffer solution further contains 3 to 8M of a protein denaturant. The method wherein the buffer solution has a pH of 2 to 4.

5 Claims, 3 Drawing Sheets

(51) Int. Cl.
*C11D 7/28* (2006.01)
*C11D 7/34* (2006.01)
*C11D 11/00* (2006.01)
 B01L 3/00 (2006.01)
 G01N 27/447 (2006.01)
 G01N 30/60 (2006.01)

(56) References Cited

U.S. PATENT DOCUMENTS

| | | |
|---|---|---|
| 8,187,442 B2 | 5/2012 | Hanafusa et al. |
| 2005/0161402 A1* | 7/2005 | Hanafusa et al. ............. 210/656 |
| 2008/0148491 A1* | 6/2008 | van Buskirk et al. ............. 8/103 |

FOREIGN PATENT DOCUMENTS

| | | |
|---|---|---|
| JP | 2005-214710 A | 8/2005 |
| JP | 2008-109927 A | 5/2008 |
| JP | 4450368 B2 | 4/2010 |
| JP | 2012-47457 A | 3/2012 |
| WO | WO-2008/013801 A2 | 1/2008 |

OTHER PUBLICATIONS

Shimadzu Corporation, "Microchip Electrophoresis System for DNA/RNA Analysis MCE-202 MultiNA Instruction Manual—Instrument and System—", 4th Chapter, Jan. 2008, pp. 17-20.

* cited by examiner (A)

(B)

(C)

(D)

METHOD FOR CLEANING MICROFLUIDIC DEVICE AND CLEANING LIQUID

BACKGROUND OF THE INVENTION

1. Field of the Invention

The present invention relates to a microchip LC or a microchip electrophoresis performed in a microfabricated microfluidic device (microchip).

The present invention relates to a method for cleaning a microchip after use and a cleaning liquid.

2. Disclosure of the Related Art

Assays utilizing characteristic gene sequences tend to increase year by year. Particularly, there is a strong demand to simply, quickly, and cheaply perform genotyping such as analysis of single or multiplex PCR products, restriction enzyme digests obtained by PCR-RFLP, or SNPs, study of PCR reaction conditions, or analysis of reaction liquids after real-time PCR measurement.

For responding such a demand, microchip electrophoresis is becoming a very suitable method instead of agarose gel electrophoresis. Microchip electrophoresis is particularly characterized in that separation/detection time is as very short as 1 to 2 minutes, high-accuracy separation for identification impossible for agarose gel electrophoresis can be achieved, and numerical data can be displayed and stored. Further, if a reaction liquid in a PCR plate can be directly set in an apparatus without being purified or diluted, operability is greatly improved.

However, a microfabricated microchip (for example, Patent Document 1: JP 2005-214710 A) is expensive, and therefore reuse is more preferable than disposal from the viewpoint of running cost.

As a method for cleaning a microchip for reuse, a method is performed in which reservoirs and channels of the microchip are cleaned every time the electrophoresis of a sample is finished to remove a running buffer, a separation medium, the sample, etc (for example, Non-Patent Document 1: Microchip Electrophoresis System for DNA/RNA Analysis, MCE-202 MultiNA, Instruction Manual, —Instrument and System—, January 2008, The fourth chapter, pp. 17-20, by SHIMADZU CORPORATION).

SUMMARY OF THE INVENTION

When an amplified product in a PCR plate is directly set in an electrophoresis apparatus and subjected to microchip electrophoresis, KCl and/or $MgCl_2$ coexist in a sample with DNA polymerase, primer DNA, animal- or plant-derived target DNA, and dNTP in order to maintain the activity of the DNA polymerase. Further, there is a case where a PCR reaction buffer contains a nonionic surfactant to effectively perform DNA amplification or previously contains a loading dye and a specific gravity-increasing agent on the precondition that agarose gel electrophoresis is used. In the case of assays using restriction enzymes, BSA, betaine, or the like is often contained. Among them, protein and basic or hydrophobic compounds contained in the sample basically tend to adsorb to the surface of a microchip, although the degree of adsorption depends on the material (e.g., glass, quartz, resin) of the surface of the microchip. Therefore, when the microchip is repeatedly used, a risk of temporal change in separation characteristics remains. On the other hand, an influence on the surface of a channel can be reduced by purifying or diluting a crude sample, but such an additional operation performed on a reaction product reduces simplicity.

The microchip is conventionally cleaned with water after use and reused. However, there is a case where the performance recovery of the microchip is insufficient due to adsorption of various components as described above.

It is therefore an object of the present invention to provide a cleaning method by which the performance of a microchip can be recovered and a cleaning liquid.

The present inventor has found that the above object of the present invention can be achieved by using a polar organic solvent-based cleaning liquid, which has led to the completion of the present invention.

The present invention includes the following.

(1) A method for cleaning a microfluidic device comprising: cleaning a channel that is formed in the microfluidic device, has a surface having a polymer coating, and has been brought into contact with a sample containing nucleic acid and/or protein, by bringing the channel into contact with a cleaning liquid comprised only of an organic solvent having solubility in at least the same volume of water at 25° C., or a cleaning liquid containing 50 vol % or more of the organic solvent in a buffer solution.

(2) The method for cleaning according to (1), wherein the buffer solution has a pH of 8 to 10.

(3) The method for cleaning according to (1) or (2), wherein the buffer solution further contains 3 to 8M of a protein denaturant.

(4) The method for cleaning according to (1), wherein the buffer solution has a pH of 2 to 4.

(5) A cleaning liquid for a microfluidic device comprised only of an organic solvent having solubility in at least the same volume of water at 25° C., or containing 50 vol % or more of the organic solvent in a buffer solution.

(6) The cleaning liquid according to (5), wherein the buffer solution has a pH of 8 to 10.

(7) The cleaning liquid according to (5) or (6), wherein the buffer solution further contains 3 to 8M of a protein denaturant.

(8) The cleaning liquid according to (5), wherein the buffer solution has a pH of 2 to 4.

According to the present invention, it is possible to provide a cleaning method by which the performance of a microchip can be recovered and a cleaning liquid.

DETAILED DESCRIPTION OF THE INVENTION

[1. Microfluidic Device (Microchip)]

Figure 1:
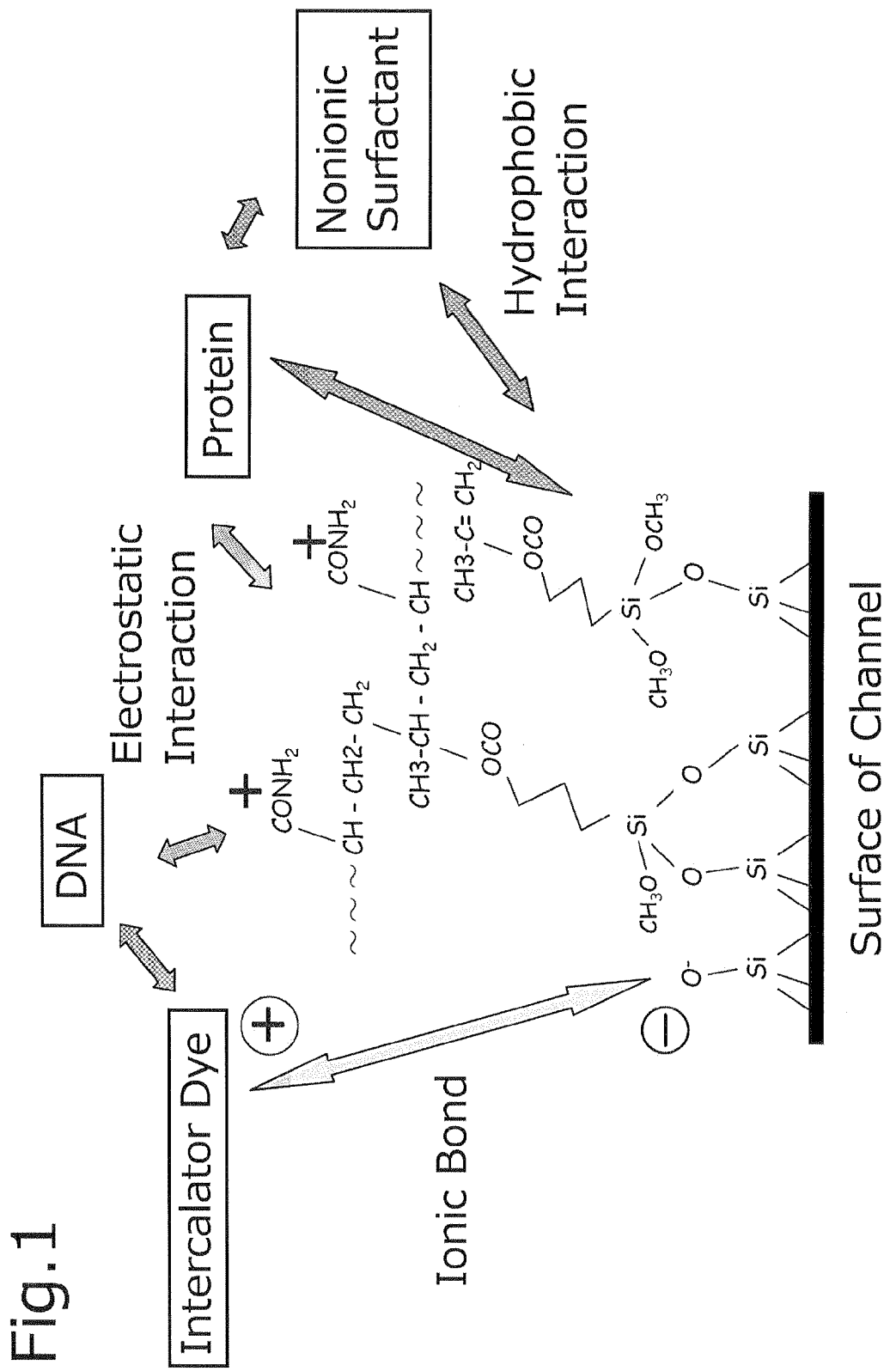
FIG. 1 schematically shows interactions between the surface of a channel of a microchip and components near the channel.

In the present invention, the channel configuration or design of a microfluidic device to be cleaned is not particularly limited as long as a liquid containing nucleic acid and/or protein can be held and transported.

A material of the microfluidic device is not particularly limited, and may be, for example, quartz, glass, or resin. The material preferably has high transparency from the viewpoint of optical characteristics. Particularly, a cleaning method and a cleaning liquid of the present invention are effective when a material having silanol groups on their surface is used.

The microfluidic device has a formed channel, and the channel is surface-treated with a polymer coating.

[1-1. Polymer Coating]

The polymer coating may have hydrophilic groups providing an environment in which a sample containing nucleic acid and/or protein is separated, and may protect the surface of the channel from interaction with a sample and/or a separation buffer. When a sample containing nucleic acid and/or protein is subjected to electrophoretic separation in the channel, the polymer coating may also be intended to suppress electroosmotic flow. When a sample containing nucleic acid and/or protein is subjected to chromatographic separation in the channel, the polymer coating may also be a carrier for separation or a stationary phase for separation.

The polymer coating may be either adsorbed to or covalently bonded to the surface of the channel. When the polymer coating is formed by covalent bonding to the surface of the channel, in one aspect of such a coating, one of functional groups of a bifunctional compound is covalently bonded to the surface of the channel, and the other functional group of the bifunctional compound is covalently bonded to a polymer forming an organic coating (monomolecular film). Such a polymer coating may be formed by bringing the bifunctional compound into contact with the surface of the channel to covalently bond one of its functional groups to the surface, and then adding a monomer to polymerize the monomer with the other functional group. In this case, when a material having silanol groups is used for the surface of the channel, examples of the bifunctional compound include silane coupling agents such as γ-methacryloxypropyltrimethoxysilane, vinyltriacetoxysilane, vinyltri(β-methoxyethoxy)silane, vinyltrichlorosilane, methylvinyldichlorosilane, and the like. Examples of the monomer include an acrylic monomer, an acryloyl monomer, a methacrylic monomer, an allyl monomer, a vinyl monomer, and an acrylamide monomer. The monomer may further have, as a substituent, a hydrophilic group such as an amino group, a hydroxyl group, a pyrrole group, or the like. Particularly, the cleaning method and the cleaning liquid of the present invention are effective when the surface of the channel has a copolymer coating having a pKa of 8 to 10, because electrification of the polymer coating can be suppressed to prevent the adsorption of components within the channel due to electrostatic interaction.

When the polymer coating is formed by the adsorption to the surface of the channel, such a polymer coating may be formed by applying a polymer onto the surface of the channel, or by adsorbing a polymer to the surface of the channel simply by mixing the polymer into a separation buffer and bringing the separation buffer into contact with the surface of the channel.

Also in the microfluidic device where liquid chromatography is performed, in addition to a carrier for separation obtained by chemically bonding a silylation agent having a hydrophobic functional group to silanol groups on the surface of the channel, a coating made of a water-soluble polymer for the purpose of improving alkali resistance or reducing adsorption of protein can be applicable. Examples of the water-soluble polymer include methyl cellulose, polyoxyethylene, and the like.

[1-2. Channel]

The microfluidic device is not always limited to be small in size as long as it has a channel. The channel may generally include a main channel where migration and analysis of a solution are performed. Examples of the channel include an electrophoresis channel including a separation channel where an electrophoresis process is performed, a liquid-sending channel including a separation carrier where a liquid chromatography process is performed, and a liquid-sending channel having a surface modification as a stationary phase for separation. Further, a sample and/or mobile phase introduction channel connected to the main channel may be provided. Each of these channels may be provided in a plural manner.

[1-3. Specific Example]

Figure 2:
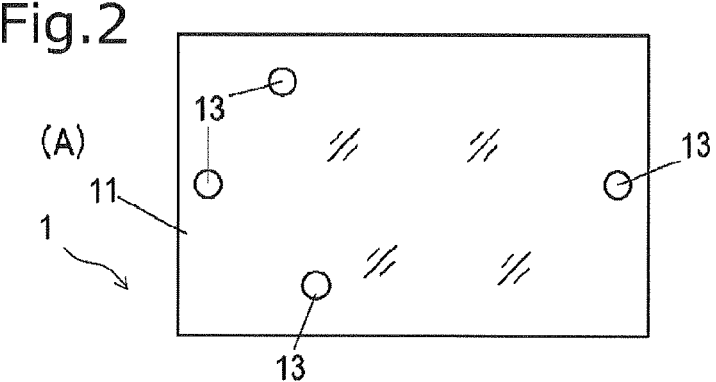
FIG. 2 shows one example of a microchip to be cleaned.
Figure 2:
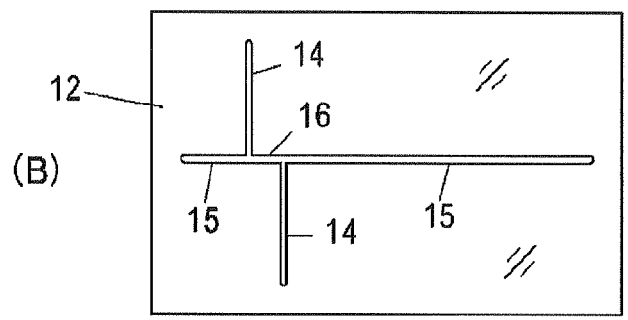
Figure 2:
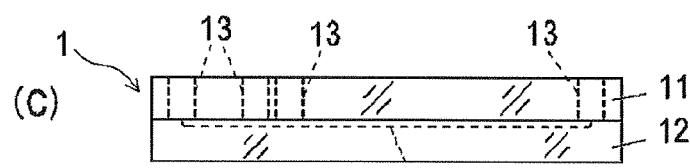
Figure 2:
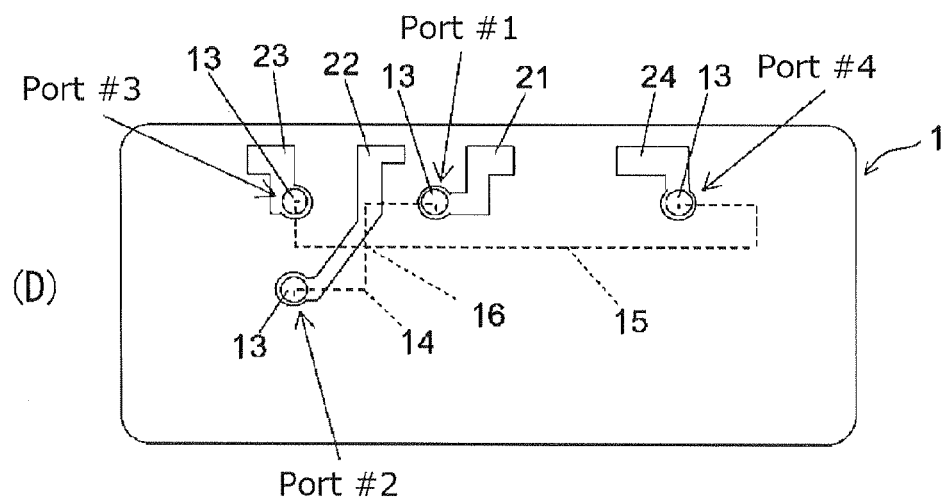

FIG. 2 shows a microchip for electrophoresis as one example of the microfluidic device.

As shown in FIG. 2, a microchip 1 comprises a pair of transparent substrates (substrates made of glass such as quartz glass or resin substrates) 11 and 12. As shown in FIG. 2(B), capillary grooves for migration 14 and 15 crossing each other are formed in the surface of one substrate 12. As show in FIG. 2(C), through holes are formed as reservoirs 13 in the other substrate 11 at positions corresponding to the ends of the grooves 14 and 15. As shown in FIG. 2(C), both the substrates 11 and 12 are stacked and joined together so that the capillary groove 15 functions as a separation channel 15 for electrophoretic separation of a sample and the capillary groove 14 functions as a sample introduction channel 14 for introducing a sample into the separation channel.

The microchip 1 is basically a microchip shown in FIGS. 2(A) to 2(C). However, as shown in FIG. 2(D), the microchip 1 may be one having electrode terminals previously provided thereon to apply a voltage for ease of handling (which will be described later in examples).

[2. Adsorption of Components Derived from Sample, Etc.]

The present invention is applied to a used microfluidic device. The use history of the microfluidic device is not particularly limited as long as an electrophoresis buffer containing a separation medium and/or an intercalator fluorescent dye has been enclosed, or a sample containing nucleic acid and/or protein has been brought into contact with the surface of the channel. The nucleic acid and/or protein may be an object to be analyzed. The sample may be brought into contact with the surface of the channel together with a mobile phase or a separation buffer during analysis.

[2-1. Components to be Adsorbed]

A nucleic acid-containing sample and a mobile phase may contain a buffer solution containing, in addition to nucleic acid (DNA, RNA) as an object to be analyzed, components such as a nucleic acid component other than the object to be analyzed, an enzyme, a stabilizer, a specific gravity-increasing agent, and a fluorescent dye together with a salt. These components may adsorb to the surface of the channel of the microfluidic device as impurities.

More specifically, examples of the enzyme include reverse transcriptase, DNA polymerase, restriction enzymes, and the like.

Examples of the nucleic acid component other than the object to be analyzed include template DNA, primer DNA, dNTP (dATP, dTTP, dGTP, dCTP, dUTP), and the like.

Examples of the stabilizer include glycerol, a protein, a surfactant, betaine, and the like. Examples of the surfactant include Tween 20, Nonidet P-40, Brij-35, Triton X-100, and the like. An example of the protein as the stabilizer includes BSA.

Examples of the fluorescent dye include loading dyes such as bromophenol blue, xylene cyanol, orange G, and the like. Examples of the intercalator include ethydium bromide, SYBR Gold, SYBR Green, SYBR Safe, GelStar, and the like.

The nucleic acid-containing sample may be obtained as a result of, for example, a nucleic acid amplification reaction. The nucleic acid amplification reaction is typified by PCR, but various other reactions are known to those skilled in the art. For example, in the case of PCR, its variations include normal PCR, PCR-RFLP, quantitative PCR (real-time PCR) RT-PCR, colony PCR, and any other aspects. The scale (amount) of a reaction liquid or the amount of an amplified product is not particularly limited, either. The nucleic acid-containing sample may be obtained by performing a purification process and/or a dilution process after the nucleic acid amplification reaction, or may be obtained without performing such processes.

[2-2. Estimated Mechanism of Adsorption]

A description will be made with reference to a case where DNA molecules are separated by electrophoresis in a channel formed in a microfluidic device. When a sample containing DNA molecules and a separation buffer are brought into contact with the surface of the channel, the DNA molecules basically migrate due to the negative charge of DNA without interacting with the surface of the channel while binding to a fluorescent dye that may act as an intercalator, and are separated by the sieving effect of a water-soluble polymer contained in the separation buffer. In this case, as schematically shown in, for example, FIG. 1, various components present in the channel may be adsorbed due to various possible interactions with the surface of the channel and/or between the above-mentioned components. FIG. 1 schematically shows interactions between the surface of a channel and components containing a DNA-containing sample and a separation buffer, when the sample is subjected to electrophoresis using the separation buffer with a pH of 8.3 in a microfluidic device having a channel whose surface has silanol groups and is covered with a linear polyacrylamide (LPA) coating obtained by a radical copolymerization reaction between the organic functional group of γ-methacryloxypropyltrimethoxysilane used as a silane coupling agent and acrylamide.

When migration is performed under the condition of, for example, pH 8.3, SYBR Gold in the buffer may be adsorbed by ionic bonding or basic components may be adsorbed because free silanol groups remain on the surface of the channel. An enzyme, a nonionic surfactant that may be contained as a stabilizer for PCR reaction, or BSA may be adsorbed by hydrophobic interaction with the silane coupling agent covalently bonded to the surface of the channel.

Further, linear polyacrylamide (LPA) is considered to have a pKa of 8.0 to 10.0, and it is estimated that LPA is put into a state where it may have a positive charge by a buffer with a pH of about 8 or cleaning with water and DNA molecules or BSA may be electrostatically adsorbed.

The estimated mechanism of adsorption shown in FIG. 1 illustrates only main interactions. In fact, it is considered that components (e.g., glycerol, a restriction enzyme) other than the components shown in FIG. 1 coexist in the channel and various interactions occur.

[3. Cleaning Liquid]

[3-1. Polar Organic Solvent-Based Cleaning Liquid]

In order to remove the adsorbed components, in the present invention, a cleaning liquid comprised of a 100% polar organic solvent, or a cleaning liquid obtained by dissolving a polar organic solvent of 50 vol % or more, and preferably 70 vol % or more in water or a buffer solution is brought into contact with the surface of the channel. When the amount of the polar organic solvent is less than the above range, the cleaning effect of the present invention is less likely to be obtained.

The polar organic solvent in the present invention has solubility in at least the same volume of water at 25° C. Specific examples thereof include alcohol and/or acetonitrile. As the alcohol, methanol, ethanol, isopropyl alcohol, or the like is particularly used.

Such a cleaning liquid can reduce hydrophobic interaction, and therefore can remove, for example, protein or a stabilizer that may interact with the hydrophobic part of the silane coupling agent on the surface of the channel.

[3-2. Alkaline Cleaning Liquid]

When the above-described cleaning liquid contains a buffer solution, the buffer solution may have a pH of, for example, 8 to 10, and preferably 8.3 to 8.9.

Examples of the buffer solution to be used include tris-hydrochloric acid buffer, tris-acetic acid buffer, HEPES (2-[4-(2-hydroxyethyl)-1-piperazinyl]-ethanesulfonic acid) buffer, MOPS (morpholinepropanesulfonic acid) buffer, TAPS (N-[tris(hydroxymethyl)methyl]-3-aminopropanesulfonic acid) buffer, phosphate buffer, and the like.

In the alkaline range of pH 8 to 10, electrification of the polymer coating on the surface of the channel may be suppressed, and therefore, a nucleic acid component (e.g., DNA), protein (e.g., BSA) or the like that may electrostatically interact with the surface of the channel can be removed. If the pH of the buffer solution is less than the above range, the above-described effect is less likely to be obtained. If the pH of the buffer solution exceeds the above range, the hydrolysis of the silane coupling agent occurs, which may tend to cause irreversible damage to the polymer coating.

This cleaning liquid can be basically used for any microfluidic device having the use history exemplified in this specification.

[3-3. Denaturant-Containing Cleaning Liquid]

The above-described cleaning liquid may further contain a denaturant. Examples of the denaturant include urea and a guanidine salt that destroy the stability of hydrogen bond. Examples of the guanidine salt include guanidine hydrochloride, guanidine isothiocyanate, and the like. The concentration of the denaturant may be 3 to 8M, and preferably 6 to 8M in the buffer solution. The concentration of the denaturant may also be 3 to 8M, or 6 to 8M in a mixture liquid of the organic solvent and the buffer solution. When the guanidine salt is used, dithiothreitol as a reducing agent may coexist with the guanidine salt.

Such a denaturant allows protein to lose its higher-order structure and dissociate into polypeptide chains, which makes it possible to reduce adsorption of protein. Therefore, the cleaning liquid containing such a denaturant can remove protein (e.g., BSA, an enzyme) that may adsorb to the surface of the channel.

However, caution should be exercised because too high a salt concentration makes it difficult to prepare a cleaning liquid, and in addition, there is a fear that when crystals are left, a fine channel is clogged with the crystals.

[3-4. Acidic Cleaning Liquid]

On the other hand, when the above-described cleaning liquid contains a buffer solution, the buffer solution may have a pH of, for example, 2 to 4, and preferably 2.5 to 3.5.

In the acidic range, dissociation of the silanol groups remaining on the surface of the channel is suppressed, and therefore, the acidic cleaning liquid can remove a fluorescent dye or a basic compound with a positive charge that may be ionically-bonded to dissociated silanol groups on the surface of the channel.

When the pH of the buffer solution is less than the above range, there is a possibility that hydrolysis of amide occurs in polyacrylamide so that a polycarboxylic acid structure is formed, which has an influence on separation characteristics (selectivity).

[4. Cleaning Method]

A cleaning method is not particularly limited as long as the cleaning liquid can be brought into contact with the surface of the channel. The channel may be filled with the cleaning liquid in the same way that a sample, a mobile phase, and/or a separation buffer is introduced into the microfluidic device. Examples of the cleaning method include a method in which a certain volume of the cleaning liquid is allowed to continuously flow through the channel of the device by means of pressure feeding such as a pump and a method in which the cleaning liquid is pressure-fed by the above-described means to fill the channel with the cleaning liquid and then the device is immersed in the cleaning liquid for a certain period of time.

The time of cleaning is not particularly limited. However, in order to effectively remove components adsorbed to the surface of the channel, in the case of the above-described liquid feeding method, the cleaning liquid is allowed to flow at a flow rate of, for example, 20 to 500 μL/minute for 0.1 to 4 hours, and preferably 50 μL/minute for 1 to 2 hours, and in the case of the above-described immersion method, the device is immersed for, for example, about 2 to 48 hours, and preferably about 6 to 18 hours.

The temperature upon cleaning is not particularly limited, and cleaning can be performed at room temperature (e.g., 20° C.±15° C.)

The number of times and frequency of cleaning (i.e., how many times it is appropriate to perform cleaning after how many times the microfluidic device is used for analysis) are not particularly limited because the components and amount thereof remaining on the surface of the channel may vary depending on the composition of the sample and the mobile phase or the separation buffer. For example, cleaning may be regularly performed every time the microfluidic device is used several tens to several hundreds of times (e.g., 20 to 500 times).

More specifically, for example, in the case of a normal nucleic acid amplification reaction (PCR reaction scale: 50 μL, amount of amplified product: about 5 ng/μL), cleaning may be performed according to the present invention after the microfluidic device is used about 100 to 500 times while being regenerated by cleaning with water. When the amount of an amplified product is large (50 ng/μL or more), especially when the amount of polymerase with high adsorption tendency is large or when the concentration of a stabilizer or a specific gravity-increasing agent is high, cleaning may be performed according to the present invention every time analysis is performed once or several tens of times (e.g., 20 to 50 times).

An apparatus may incorporate automatic cleaning function to regularly perform cleaning a predetermined number of times at a predetermined frequency to handle cleaning on a time schedule. By regularly performing cleaning, it is possible to maximally maintain the performance of the microfluidic device.

The cleaning liquid can be selected depending on components considered to be adsorbed. At this time, the selection can be made based on the above description in [3-1] to [3-4].

EXAMPLES

Hereinbelow, the present invention will be described in more detail byway of examples. However, the present invention is not limited to the following examples. In the following description, "%" used to represent the composition of a cleaning liquid refers to a volume percentage.

[1. Microfluidic Device (Microchip)]

One hundred and thirty five (total number) microchips having degraded performance due to repeated use for electrophoretic analysis of nucleic acid-containing samples were prepared as test samples. More specifically, the microchip is one schematically shown in FIG. 2(D). FIG. 2(D) shows a plan view of a microchip 1 used. The microchip 1 is composed of quartz substrates, and reservoirs 13 also serve as ports for applying a voltage to channels 14 and 15. Ports #1 and #2 are ports located at both ends of the sample introduction channel 14, and ports #3 and #4 are ports located at both ends of the separation channel 15. In order to apply a voltage to the ports, respectively, electrode patterns 21 to 24 formed on the surface of the chip 1 extend from their respective ports toward the side edge of the microchip 1 to connect to a high-voltage power supply for electrophoresis. The inner walls of the channels 14 and 15 have an LPA coating provided on their surfaces with γ-methacryloxypropyltrimethoxysilane interposed therebetween as a silane coupling agent.

Regarding the use histories of the prepared 135 microchips, 123 microchips out of the 135 microchips had been used for the analysis of nucleic acid-containing samples. The kinds of analysis to which the 123 microchips were subjected were classified into the following five categories:
i) analysis of normal amount of PCR product (using reaction system containing no BSA);
ii) analysis of normal amount of PCR product (using reaction system containing BSA);
iii) analysis of product obtained by PCR-RFLP (unrefined and undiluted);
iv) analysis of large amount of PCR product (using reaction system containing excessive polymerase); and
v) analysis using excessive amount of SYBR Gold as intercalator.

The normal amount of PCR product is about 5 ng/μL, and the large amount of PCR product (e.g., multiplex PCR product) is 50 ng/μL or more. The excessive polymerase refers to polymerase in an amount required to construct a PCR system to generate the above-described large amount of PCR product. The excessive amount of intercalator refers to an intercalator having a concentration higher than, for example, 10,000-fold dilution.

Twenty nine microchips randomly selected from the 123 microchips were cleaned with a cleaning liquid A, 25 microchips randomly selected therefrom were cleaned with a cleaning liquid B, 47 microchips randomly selected therefrom were cleaned with a cleaning liquid C, and 22 microchips randomly selected therefrom were cleaned with a cleaning liquid ID (the composition of each of the cleaning liquids will be described later). However, 5 out of the 22 microchips cleaned with the cleaning liquid D failed to recover performance by cleaning with the cleaning liquid C.

The analysis to which the remaining 12 out of the 135 microchips were subjected is the electrophoretic analysis of purified DNA ladders for electrophoretic analysis of nucleic acid, or electrophoretic analysis of standard substances for electrophoretic analysis of nucleic acid. These 12 microchips were cleaned with a cleaning liquid E.

[2. Cleaning Liquid]

The cleaning liquids A to E having the following composition were prepared.
A: methanol 100%
B: ethanol 100%
C: ethanol 70% and 10 mM TAPS-NaOH buffer containing 1 mM EDTA (pH 8.9) 30%
D: ethanol 70% and 10 mM TAPS-NaOH buffer containing 1 mM EDTA and 8M guanidine-HCl (pH 8.9) 30%
E: acetonitrile 70% and 20 mM phosphate (Na) buffer containing 0.1 M $NaClO_4$ (pH 2.5) 30%

[3. Procedure of Channel Cleaning]

The cleaning with the cleaning liquid A was performed by a liquid feeding method. The cleaning by a liquid feeding method was performed according to a procedure of feeding the cleaning liquid A from the port #4 to the ports #1 to #3 with the use of a liquid feeding pump (e.g., a pump for liquid chromatography or a syringe pump) at a constant flow rate of 50 μL/minute for 80 minutes.

The cleaning with the cleaning liquid B, C, D, or E was performed by an immersion method. The cleaning by an immersion method was performed according to the following procedure.
(1) 0.2 mL of the cleaning liquid was injected under pressure from the port #4 of the chip by a 1 mL disposable syringe.
(2) The chip was immersed in the cleaning liquid contained in a Falcon tube (10 mL or 50 mL) without sucking the cleaning liquid overflowing the ports #1 to #3.
(3) The chip was allowed to stand as it was for 18 to 24 hours.
(4) The chip was taken out of the cleaning liquid, and then 0.2 mL or more of Milli-Q water was injected under pressure from the port #4 by a 1 mL disposable syringe. The overflowed water was removed by suction and the surface of the chip was wiped with BEMCOT (when BEMCOT did not slide easily on the quartz surface due to a residual salt on the surface of the chip, the surface was again gently wiped with water).
(5) The chip was set in a chip frame and cleaned the chip on MultiNA.

[4. Performance Evaluation]

Performance evaluation was performed on the chips in the groups (a) and (b) using a microchip electrophoresis unit MultiNA manufactured by SHIMADZU CORPORATION under analysis conditions of DNA-1000 on-chip mode and TE buffer blank analysis (6 analyses/chip).

The details of the analysis conditions are as follows.

Reagent kit to be used: DNA-1000 manufactured by SHIMADZU CORPORATION (DNA size range for application: 100 bp to 1000 bp)

Analysis mode: on-chip mixing mode (analysis mode in which a sample and internal standard markers are automatically mixed on a chip)

Sample used for performance evaluation: TE buffer (used for blank analysis to detect only two peaks of 2 internal standard markers (low-molecular-weight internal standard marker and high-molecular-weight internal standard marker))

Number of analyses: 24 analyses (6 analyses/chip) (up to 4 chips can be set in the unit, and a schedule was set to repeatedly perform 6 analyses per chip using 4 chips by turns)

[5. Cleaning Effect]

Table 1 shows the cleaning effect of each of the cleaning liquids based on a recovery rate (%) (i.e., a ratio of the number of chips whose performance has been recovered to the number of chips subjected to cleaning), the average number of theoretical plates (av.) of peak of the high-molecular-weight internal standard, and migration time (average value).

The definition of the performance recovery of the microchip is that the number of theoretical plates of peak of the high-molecular-weight internal standard (hereinafter, also referred to as UM) is 80,000 or more and the migration time of UM (i.e., the time from the start of separation to the detection of the peak of UM) is 123 seconds or less. When the chip maintains its initial performance without performance degradation, the number of theoretical plates of the peak of UM is 80,000 or more and the migration time is 113±10 seconds under the above-described conditions for performance evaluation.

TABLE 1

Cleaning effect of each of Cleaning liquids

| | Cleaning liquid | A | B | C | D | E | Total |
|---|---|---|---|---|---|---|---|
| Before Cleaning | Number of Samples | 29 | 25 | 47 | 22 | 12 | 135 |
| | Number of Theoretical plates (av.) | 25371 | 29313 | 49746 | 54244 | 22627 | 38225 |
| | Migration time (sec) | 123.0 | 122.1 | 121.2 | 119.4 | 114.0 | 119.9 |
| After Cleaning | Number of Recovered Sample (Recovery rate) | 15 (52%) | 11 (44%) | 42 (91%) | 16 (73%) | 6 (50%) | 90 (67%) |
| | Number of Theoretical plates (av.) | 94808 | 79719 | 117388 | 99210 | 76385 | 96699 |
| | Migration time (sec) | 118.1 | 118.0 | 117.0 | 118.1 | 108.2 | 115.9 |

Figure 3:
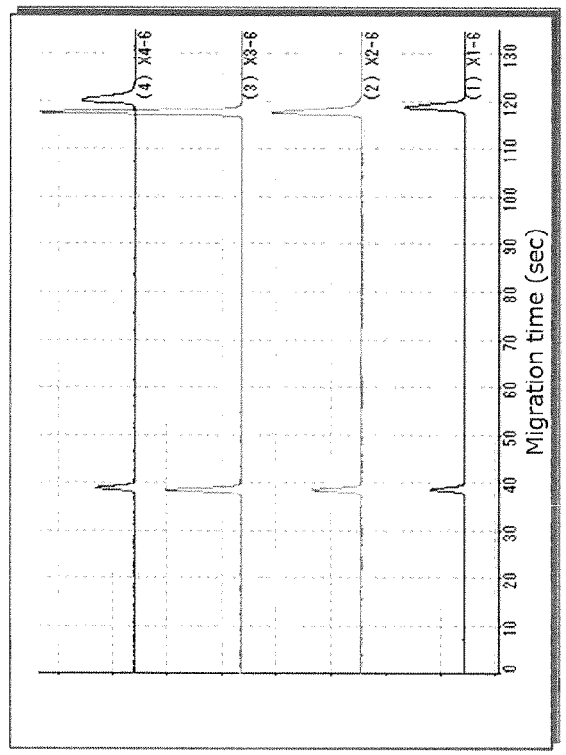
FIG. 3 shows electropherograms for comparison between before and after cleaning of microchips.
Figure 3:
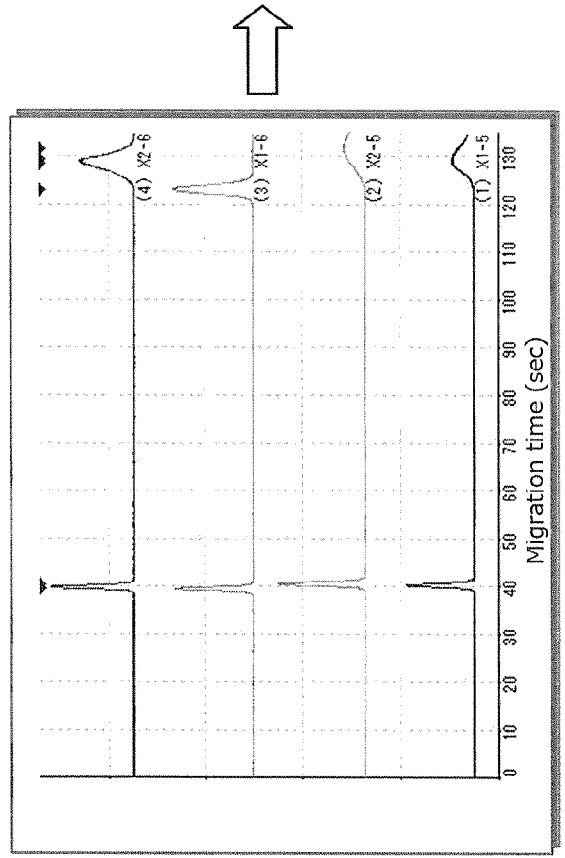

FIG. 3 shows electropherograms for comparison between before and after cleaning. FIG. 3 shows the case using the cleaning liquid C among the cases described in Table 1. The four pherograms correspond to four microchips, and the first peak represents the low-molecular-weight internal standard marker and the second peak represents the high-molecular-weight internal standard marker. Before cleaning, the second peak is broad and the migration time is long and variation among the chips is wide, but after cleaning, peak broading has been improved and the migration time is short and uniform.

(a) (Evaluation Results of Cleaning with Cleaning Liquid A)

Fifteen out of the 29 chips recovered performance. Further, the migration time of UM was improved from a tendency to be long of 123.0 seconds on average before cleaning to 118.1 seconds on average.

(b) (Evaluation Results of Cleaning with Cleaning Liquid B)

Eleven out of the 25 chips recovered performance. Further, the migration time of UM was improved from 122.1 seconds on average before cleaning to 118.0 seconds on average.

From the results (a) and (b), a recovery rate of about 50% was achieved by cleaning with a 100% polar organic solvent. From these results, it is supposed that components adsorbed to the surface of the channel mainly by hydrophobic interaction could be removed.

(c) (Evaluation Results of Cleaning with Cleaning Liquid C)

Forty two out of the 47 chips recovered performance. Further, the migration time of UM was improved from 121.2 seconds on average to 117.0 seconds, and a recovery rate of 91% was achieved. From these results, it is supposed that, in addition to the removal of adsorbed components by hydrophobic interaction with the polar organic solvent, the removal of adsorbed components by electrostatic interaction could be also effectively performed by changing pH to alkaline.

(d) (Evaluation Results of Cleaning with Cleaning Liquid D)

Sixteen out of the 22 chips recovered performance. The migration times of UM before and after cleaning were 119.4 seconds on average and 118.1 seconds, respectively, and therefore, there was no particularly significant difference.

The 22 chips include 5 chips whose performance was not recovered by the cleaning liquid C, but the performance of all the 5 chips was recovered by the cleaning liquid D. From these results, it is supposed that a protein component (e.g., BSA and/or a restriction enzyme) contained in the sample component was dissociated into polypeptide chains by the denaturant and as a result the cleaning effect was improved.

(e) (Evaluation Results of Cleaning with Cleaning Liquid E)

Six out of the 12 chips recovered performance. Further, the migration time of UM was reduced from 114.0 seconds on average to 108.2 seconds. As described above, these 12 chips subjected to cleaning with the cleaning liquid E have no history for analysis of nucleic acid-containing samples such as PCR products, PCR-RFLP products, or the like. From these results, it is supposed that treatment (pH 2.5) to suppress ionic binding to silanol groups had a certain effect on the microchips whose performance degradation is considered to be caused mainly by the adsorption of SYBR Gold contained in a separation buffer.

The above results indicated that the organic solvent-based cleaning liquids remove adsorbed components derived from the samples, and have a certain effect on the recovery of the chips whose performance has temporarily degraded.

Further, the number of test samples was increased to 427, and these test samples were subjected to the cleaning method of the present invention in the same manner. Table 2 shows an outline of the microchip cleaning method according to the present invention. As cleaning liquids, the cleaning liquids B to E were used. The microchips subjected to cleaning were microchips subjected to the analyses of the above-described categories i) toy) in their use history. The degree of cleaning effect of each of the cleaning liquids B to E on the microchips was summarized according to their use history. The case "remarkably effective" means that the recovery rate was 50% or higher, the case "effective" means that the recovery rate was 25 to 50%, and the case "no significance" means that the recovery rate was 25% or less. Based on Table 2, an appropriate composition of the cleaning liquid can be selected by those skilled in the art according to the use history of a microchip.

TABLE 2

Outline of Microchip cleaning method

| | | Cleaning liquid | | | |
|---|---|---|---|---|---|
| | | B | C | D | E |
| Use history of Microchip | i) | ++ | ++ | + | − |
| | ii) | − | + | ++ | NA(Not evaluated) |
| | iii) | − | + | ++ | NA(Not evaluated) |
| | iv) | + | ++ | + | NA(Not evaluated) |
| | v) | − | + | − | ++ |
| Number of Samples | | 54 | 282 | 38 | 53 |

++: Remarkably effective
+: Effective
−: No significance

What is claimed is:

1. A method for cleaning a microfluidic device, said method comprising:
cleaning a channel that is formed in the microfluidic device by bringing the channel into contact with a cleaning liquid comprised only of an organic solvent having solubility in at least the same volume of water at 25° C., or a cleaning liquid containing 50 vol % or more of the organic solvent in a buffer solution,
wherein the channel (1) has a surface having a silanol group thereon and a polymer coating covalently bonded to the surface, and (2) has been brought into contact with a sample containing nucleic acid and/or protein as an object to be analyzed and an impurity other than the object to be analyzed.

2. The method for cleaning according to claim 1, wherein the buffer solution has a pH of 8 to 10.

3. The method for cleaning according to claim 1, wherein the buffer solution further contains 3 to 8M of a protein denaturant.

4. The method for cleaning according to claim 1, wherein the buffer solution has a pH of 2 to 4.

5. The method for cleaning according to claim 1, wherein the polymer coating is covalently bonded to the surface of the channel via a silane coupling agent and the silanol group on the surface.

* * * * *